(12) United States Patent
Blin et al.

(10) Patent No.: US 10,220,223 B2
(45) Date of Patent: *Mar. 5, 2019

(54) COSMETIC COMPOSITION WITH A VOLUMIZING EFFECT

(71) Applicant: L'OREAL, Paris (FR)

(72) Inventors: Xavier Blin, Paris (FR); Audrey Ricard, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,193

(22) Filed: Mar. 24, 2016

(65) Prior Publication Data

US 2016/0199274 A1    Jul. 14, 2016

Related U.S. Application Data

(63) Continuation of application No. 11/639,235, filed on Dec. 15, 2006.

(60) Provisional application No. 60/757,851, filed on Jan. 11, 2006.

(30) Foreign Application Priority Data

Dec. 21, 2005 (FR) .................................... 05 13076

(51) Int. Cl.
| | | |
|---|---|---|
| *A61K 8/34* | (2006.01) | |
| *A61K 8/37* | (2006.01) | |
| *A61Q 1/02* | (2006.01) | |
| *A61Q 1/04* | (2006.01) | |
| *A61Q 1/06* | (2006.01) | |
| *A61Q 19/00* | (2006.01) | |

(52) U.S. Cl.
CPC ............... *A61Q 1/04* (2013.01); *A61K 8/345* (2013.01); *A61K 8/375* (2013.01); *A61Q 1/02* (2013.01); *A61Q 1/06* (2013.01); *A61Q 19/00* (2013.01)

(58) Field of Classification Search
CPC ........ A61K 8/345; A61K 8/375; A61Q 19/00; A61Q 1/02; A61Q 1/04; A61Q 1/06
See application file for complete search history.

(56) References Cited

U.S. PATENT DOCUMENTS

| | | | |
|---|---|---|---|
| 4,002,775 A | 1/1977 | Kabara | |
| 4,150,052 A * | 4/1979 | Watson | A23G 3/36 546/226 |
| 4,335,104 A | 6/1982 | VanCleave | |
| 4,659,562 A | 4/1987 | Arraudeau et al. | |
| 4,959,369 A * | 9/1990 | Salim | A61K 31/195 514/263.31 |
| 5,252,714 A | 10/1993 | Harris et al. | |
| 5,690,919 A | 11/1997 | Rockl et al. | |
| 5,725,845 A * | 3/1998 | Krog | A61K 8/0229 424/401 |
| 5,874,069 A | 2/1999 | Mendolia et al. | |
| 5,919,441 A | 7/1999 | Mendolia et al. | |
| 5,972,320 A | 10/1999 | Moloney et al. | |
| 5,981,680 A | 11/1999 | Petroff et al. | |
| 6,051,216 A | 4/2000 | Barr et al. | |
| 6,123,953 A | 9/2000 | Greff | |
| 6,153,567 A * | 11/2000 | Hughes | A61K 8/22 252/186.27 |
| 6,264,962 B1 | 7/2001 | Breton et al. | |
| 6,270,811 B1 | 8/2001 | Fregonese | |
| 6,333,053 B1 * | 12/2001 | Simon | A61K 8/8147 424/401 |
| 6,423,329 B1 * | 7/2002 | Sine | A61K 8/26 424/401 |
| 2004/0029946 A1 * | 2/2004 | Arora | A61K 9/0014 514/406 |
| 2004/0081679 A1 * | 4/2004 | Simon | A61K 8/0208 424/443 |
| 2004/0086619 A1 * | 5/2004 | Zhong | A23L 2/385 426/590 |
| 2004/0258783 A1 | 12/2004 | Millou et al. | |
| 2005/0048139 A1 * | 3/2005 | Modak | A61K 8/27 424/725 |
| 2005/0171194 A1 | 8/2005 | Yu et al. | |
| 2005/0238602 A1 | 10/2005 | Modak et al. | |

(Continued)

FOREIGN PATENT DOCUMENTS

| | | |
|---|---|---|
| DE | 2 204 943 A1 | 8/1973 |
| DE | 195 41 967 A1 | 5/1997 |

(Continued)

OTHER PUBLICATIONS

Yves Saint Laurent (Yves Saint Laurent Top Secrets Lip Re-Plumping Concentrate, http://www.cosmetic-ingredients.net/product.php?brand=120&type=Treatment&lang=English#16245, Printed on Jan. 27, 2018).*

Nowara et al.; Journal of Agricultural and Food Chemistry; 1997; pp. 1459-1463; vol. 45.

Science Toys, Silicone, Oct. 28, 2003; pp. 1-3; http://sci-toys.com/ingredients/dimethicone.html; retrieved online on Aug. 25, 2010.

Cornwell et al.; Glyceryl Monocaprylate.Caprate as a Moderate Skin Penetration Enchancer; International Journal of Pharmaceutics; 1998; pp. 243-255; vol. 171.

Michalun; Skin Care and Cosmetics Ingredients Dictionary; 1994; pp. 1-3; Milady Publishing Company.

(Continued)

*Primary Examiner* — Mark V Stevens
(74) *Attorney, Agent, or Firm* — Oliff PLC

(57) ABSTRACT

A cosmetic composition for caring for and/or making up the skin and/or the lips, containing, in a physiologically acceptable medium, includes at least:
  one active agent comprising at least one glycol with a $C_4$-$C_{16}$ hydrocarbon-based chain and/or a hydroxylated ester resulting from the esterification of polyol and/or of $C_4$-$C_{16}$ carboxylic acid(s), and
  one additional agent chosen from essential oils, agents for promoting capillary circulation and temperature regulators, and mixtures thereof.

23 Claims, No Drawings

(56) References Cited

U.S. PATENT DOCUMENTS

| | | | |
|---|---|---|---|
| 2006/0106024 A1* | 5/2006 | Levy | A01N 43/80 514/250 |
| 2006/0153886 A1* | 7/2006 | Leigh | A61K 8/0279 424/401 |
| 2006/0165644 A1 | 7/2006 | Tanaka et al. | |

FOREIGN PATENT DOCUMENTS

| | | |
|---|---|---|
| EP | 0 013 390 A2 | 7/1980 |
| EP | 0 225 639 A2 | 6/1987 |
| EP | 0 667 146 A1 | 8/1995 |
| EP | 0 775 478 A1 | 5/1997 |
| EP | 0 821 948 A2 | 2/1998 |
| EP | 0 847 752 A1 | 6/1998 |
| EP | 1 008 339 A1 | 6/2000 |
| EP | 1 206 933 A1 | 5/2002 |
| FR | 2 857 222 A1 | 1/2005 |
| JP | S60-179064 A | 9/1985 |
| JP | 2005-029512 A | 2/2005 |
| WO | 94/06401 A1 | 3/1994 |
| WO | 98/22075 A2 | 5/1998 |
| WO | 00/01351 A1 | 1/2000 |
| WO | 01/12150 A1 | 2/2001 |
| WO | 01/85104 A1 | 11/2001 |
| WO | 02/17923 A1 | 3/2002 |
| WO | 02/39971 A2 | 5/2002 |
| WO | 03/035080 A2 | 5/2003 |
| WO | 2004/016236 A1 | 2/2004 |

OTHER PUBLICATIONS

Römpp Chemie Lexikon; keyword "α-Bisabolol;" Online Version 3.5; Nov. 2003; http://www.roempp.com/prod/roempp.php.
Römpp Chemie Lexikon; keyword: "Salicylsäureester;" Online Version 3.5; Aug. 2004; http://www.roempp.com/prod/roempp.php.
Römpp Chemie Lexikon; keyword: "Lippenpflegemittel;" Online Version 3.5; Nov. 2003; http://www.roempp.com/prod/roempp.php.
Sep. 10, 2009 Opposition Draft filed by Henkel AG & Co. KgaA against European Patent No. 1 800 649 B1.

* cited by examiner

COSMETIC COMPOSITION WITH A VOLUMIZING EFFECT

This application is a continuation application of U.S. patent application Ser. No. 11/639,235 filed Dec. 15, 2006, which claims the benefit of French Application No. 05 13076 filed on Dec. 21, 2005 and U.S. Provisional Application No. 60/757,851 filed on Jan. 11, 2006, each of which is incorporated herein by reference.

The invention relates to natural makeup for the skin and/or the lips, which is pleasant to wear and is more particularly intended to reinforce its/their natural flesh tint and, as regards the lips, to give them a volumizing effect.

According to the invention, the term "natural makeup" for the skin means a means for naturally colouring the skin, as opposed to the existing means for artificially colouring the skin using self-tanning agents or melanin synthesis stimulators (pigmentation) and/or makeup agents such as dyes, pigments or specific fillers capable of giving the skin an optical coloration effect.

According to the invention, the term "natural makeup" for the lips means a means for naturally colouring the lips and/or making them look fleshy, as opposed to conventional lip makeup that uses only makeup agents such as dyes, specific pigments or reflective particles capable of giving the lips an optical coloration and/or volume effect (pouty effect).

According to the invention, the term "naturally colour" means stimulating the naturally pinkish coloration of the skin and/or the lips.

According to the invention, the term "making fleshy" means increasing the size and/or volume and/or thickness of the lips and/or remodelling them and/or making them smooth and/or giving them a more swollen or fleshy appearance.

As regards the latter effect, it is quite clear that it is a constant demand of a large number of consumers. At the present time, consumers have available only two alternatives: resorting to cosmetic surgery, or using conventional makeup compositions capable of affording such an effect by acting on optical phenomena. The first alternative may be dissuasive with regard to its invasive nature, and the second affords only a visual effect.

One of the aspects of the present invention is directed, precisely, towards obtaining cosmetic compositions that, firstly, are capable of affording a real pouty effect in terms of size and/or volume of the lips, and that, secondly, are combined with a comfort effect for the consumer.

Consequently, according to one of its aspects, the invention relates to a cosmetic composition for caring for and/or making up the skin and/or the lips, containing, in a physiologically acceptable medium, at least:
  one active agent comprising at least one glycol with a $C_4$-$C_{16}$ hydrocarbon-based chain and/or a hydroxylated ester resulting from the esterification of polyol and/or of $C_4$-$C_{16}$ carboxylic acid(s), and
  one additional agent chosen from essential oils, agents for promoting cutaneous capillary circulation and temperature regulators, and mixtures thereof.

The term "care" means non-therapeutic care capable of producing an effect without, however, preventing or correcting dysfunction of the keratin materials.

According to one embodiment of the invention, the active agent is formed from a hydroxylated ester resulting from the esterification of polyol and of $C_4$-$C_{16}$ carboxylic acid(s).

According to one embodiment of the invention, the active agent is formed from a glycol with a $C_7$-$C_{14}$ hydrocarbon-based chain.

According to one embodiment of the invention, the active agent is formed from a hydroxylated ester resulting from the esterification of polyol and of $C_4$-$C_{16}$ carboxylic acid(s) and of a glycol with a $C_4$-$C_{16}$ hydrocarbon-based chain.

The cosmetic compositions according to the invention may for example be intended for topical application.

Another aspect of the invention relates to a method for making up the skin and/or the lips, which is directed towards giving a healthy complexion effect using a composition in accordance with the invention, and also to a method for caring for and/or making up the lips, comprising the application to the lips of a composition that is also in accordance with the present invention.

The compositions according to the invention may be used to reinforce the natural flesh tint of the skin and/or the lips and/or the natural volume of the lips.

The compositions according to the invention may also be used to afford a naturally healthy complexion, for example by application to the face. The compositions may be applied daily to the entire face to obtain a uniform natural complexion. The application may also be limited to, renewed on or reinforced on the cheeks and the cheekbones, for example to accentuate the "healthy appearance" effect on particular areas of the face.

In this case, the compositions may be in the form of a skincare base, a care cream (day cream, night cream or anti-wrinkle cream), a makeup base or a tinted care cream.

The compositions according to the invention may also be used to hide or fade out skin defects, for example bags under and/or shadows around the eyes, to obtain a homogeneous, uniform complexion, of lively, light, natural appearance. They may thus make it possible to homogenize and/or clarify the complexion and/or to reduce the hazy complexion effect.

The compositions may also be used to improve the appearance of the lips or the contour of the lips, for instance to modify the coloration of the lips or to stimulate their natural coloration, to increase the volume of the lips and/or to model them and/or make them smoother. They may thus be used to make the lips fleshy, for example by increasing the size and/or volume and/or thickness of the lips and/or remodel them and/or make them smooth and/or give them a more swollen or fleshy appearance.

More generally, another aspect of the present invention relates to a cosmetic method for reinforcing the natural flesh tint of the skin and/or the lips and/or the natural volume of the lips; and/or for giving the skin, for example of the face, a healthy appearance; and/or for homogenizing and/or clarifying the complexion and/or for reducing the hazy complexion effect; and/or for increasing the size and/or volume of the lips and/or for modelling them and/or making them smoother; and/or for stimulating the natural coloration of the lips; and/or for giving a healthy complexion effect, said cosmetic method comprising at least the step of applying on skin a composition as disclosed herein.

Depending on the sites of application for which they are intended, the compositions may be a natural makeup product for the skin in the form of a skincare base or cream, a makeup base, a tinted cream, a foundation in liquid, semi-solid or powder form, an eye contour care product, a concealing care serum, a concealer stick or a natural makeup product for the lips in the form of a lipstick, a liquid gloss, a lipstick paste, a lip contour pencil, a lipcare balm or a lip varnish, also known as a lip lacquer.

Some of the active agents under consideration according to the invention are already known for their antiseptic properties and are conventionally used in this respect in compositions intended to be administered to man or animals as pharmaceutical, nutritional and cosmetic compositions. The presence of these compounds ensures stability over time for the corresponding compositions. Thus, document U.S. Pat. No. 5,690,919 describes deodorants comprising glyceride monocaprylate as antimicrobial agent. Similarly, document DE 19 54 19 67 describes aqueous solutions comprising these same esters as microbicides. More generally, U.S. Pat. No. 4,002,775 proposes the use of monoesters of polyol and a $C_{12}$ aliphatic fatty acid as microbicidal agent in compositions intended for nutritional use. These documents do not describe the combination of an additional agent with the active agents according to the invention.

For its part, the invention results from the demonstration by the inventors that the combination with the active agent of an additional agent according to the invention makes the wearing of makeup more pleasant and/or contributes towards the desired effect of the active agent.

Thus, for example concerning the lips, it has been noted that the placing in contact of the lips with the compositions according to the invention is pleasant to wear and induces a significant swelling effect capable of affording the desired fleshy effect.

Active Agent a) Glycols

The glycol used according to the invention may have a $C_4$-$C_{16}$ hydrocarbon-based chain and for example has a $C_6$-$C_{14}$, $C_7$-$C_{14}$ and better still $C_7$-$C_{10}$ hydrocarbon-based chain.

In one embodiment, in which the glycol is used without polyol ester, the glycol may, for example, have a $C_7$-$C_{14}$ hydrocarbon-based chain.

The term "glycol with a $C_x$ hydrocarbon-based chain" is intended to denote the compounds of formula (I):

in which R is a $C_{x-2}$ alkyl radical.

The glycol with a hydrocarbon-based chain may have, alone or in combination, a $C_8$-$C_{10}$ hydrocarbon-based chain.

It may for example, be caprylyl glycol and for instance the compound sold under the name Caprylyl Glycol Dermosoft Octiol from Straetmans.

The glycol(s) may be present in these compositions in a content ranging from 0.05% to 20%, from 0.1% to 10%, or less than 5% by weight, for example from 0.1% to 5%, or from 0.5% to 2% by weight relative to the total weight of the composition.

b) Esters

As esters that may be suitable according to the present invention, mention may be made for example of hydroxylated esters resulting from the esterification of polyol and of $C_4$-$C_{16}$, more particularly $C_6$-$C_{12}$, especially $C_7$-$C_{10}$ and more particularly $C_8$-$C_9$ carboxylic acid(s).

The esters used according to the invention are in a hydroxylated form, i.e. they bear at least one, for example two, or for instance three or more, hydroxyl functions, the hydroxylated functions being present on the alcohol residue of the ester.

For example, the esters are $C_{10}$-$C_{20}$ and contain at least one fatty chain.

In general, they are derived from the esterification of at least one hydroxyl function of a polyol with a $C_4$-$C_{16}$ carboxylic acid.

According to one embodiment, the esters that may be suitable for the present invention may be derived from the esterification of polyol with various carboxylic acids, provided that, of course, the ester thus obtained contains at least one and for example two free hydroxyl functions. It may be a hydroxylated monoester, a hydroxylated diester or a mixture thereof.

Polyols

For the purposes of the invention, the term "polyol" means any organic molecule comprising in its chemical structure at least two hydroxyl groups (OH).

The polyol may be a linear, branched or cyclic, saturated or unsaturated hydrocarbon-based compound bearing at least two and for example at least three OH functions.

The polyol may be for instance, a hydrocarbon-based compound bearing at least two carbon atoms and for example less than 15 carbon atoms, and bearing at least two hydroxyl groups and for instance from 2 to 10 hydroxyl groups.

For example, it is a hydrocarbon-based compound containing from 2 to 12 carbon atoms and for instance from 2 to 8 carbon atoms.

The polyol may be a compound containing from 2 to 8 carbon atoms and from 2 to 6 hydroxyl functions, such as for instance ethylene glycol, glycerol, 1,2,3-trihydroxyhexane, butanediol, 1,2-propanediol, erythritol, arabitol, adonitol or dulcitol, pentanediols and for example 1,2-pentanediol, and sorbitol, or mixtures thereof.

Glycerol derivatives are, for example, butyl diglycol, polyglyceryl-3 diisostearate and castor oil. The polyol may be selected from the group consisting of glycerol polymers and copolymers, for instance hexaglycerol and diglycerol.

Glycol derivatives are, for example, ethylene glycol, propylene glycol, hexylene glycol, isoprene glycol, butylene glycol and pentylene glycol, and those defined above.

The polyol may also be selected from the group consisting of sugars such as glucose, fructose, xylose, trehalose, sucrose, maltose and lactose, and mixtures thereof.

A mixture polyols may also be used.

The polyol used according to the invention may be selected for instance from the group consisting of glycerol and glycols, and derivatives thereof.

The polyols according to the invention may also be selected for example from the group consisting of glycerol and 1,2-propylene glycol, or a mixture of two or more of these polyols.

Carboxylic Acid

The carboxylic acid may be linear or branched, and saturated or unsaturated.

For example, it is a linear monocarboxylic acid.

As illustrations of monocarboxylic acids that are suitable for the invention, mention may be made for instance of butanoic acid, pentanoic acid, hexanoic acid, heptanoic acid, octanoic acid, nonanoic acid, decanoic acid, undecanoic acid, dodecanoic acid, tridecanoic acid, tetradecanoic acid, heptadecanoic acid, hexadecanoic acid and pentadecanoic acid.

As branched acids that may be suitable for the invention, mention may be made for example of isobutanoic acid, isopentanoic acid, pivalic acid, isohexanoic acid, isoheptanoic acid, isooctanoic acid, dimethyloctanoic acid, isononanoic acid, isodecanoic acid, isoundecanoic acid, isododecanoic acid, isotridecanoic acid, isotetradecanoic acid, isopentadecanoic acid, isohexadecanoic acid, 2-ethylhexanoic acid, 2-butyloctanoic acid and 2-hexyldecanoic acid.

Hydroxy acids such as 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytridecanoic acid, 2-hydroxytetradecanoic acid and 2-hydroxyhexadecanoic acid are also suitable for present invention.

The acid is for example a $C_7$-$C_{10}$ non-hydroxylated acid or heptanoic acid, caprylic acid or capric acid.

Esters selected from the group consisting of monoglyceryl and/or diglyceryl caprylates, monoglyceryl and/or diglyceryl heptanoates, monoglyceryl and/or diglyceryl caprates, propylene glycol caprylates and propylene glycol heptanoates, and mixtures thereof, may for example be suitable for the invention.

Thus, one ester suitable for the invention may be monoglyceryl caprylate, or mixtures thereof.

Mention may be made for example of the compounds sold under the name Capmul MCM or Akoline MCM (glyceryl caprylate/caprate) from Abitec or Dermosoft GMCY (glyceryl caprylate) from Straetmans, Capmul 708 G (glyceryl caprylate containing 75% monoesters) from Abitec and Capmul 907P (propylene glycol heptanoate) from Abitec, or alternatively Capmul 908P (propylene glycol caprylate) from Abitec.

The ester(s) may be present in these compositions in a content ranging from 0.05% to 20%, from 0.1% to 10%, or less than 5% by weight, for example from 0.2% to 5% or from 0.5% to 2% by weight relative to the total weight of the composition.

The esters may be introduced into the cosmetic compositions in accordance with the present invention according to conventional protocols.

Irrespective of the nature of the active agent, it may be present in these compositions in a content ranging from 0.05% to 20%, from 0.1% to 10%, or even less than 5% by weight, for example from 0.2% to 5% or from 0.5% to 2% by weight relative to the total weight of the composition.

Additional Agent

The additional agent may be selected from the group consisting of essential oils and from agents that promote cutaneous capillary circulation and temperature regulators, and mixtures thereof.

The essential oils may be selected from the group consisting of essential oil of cinnamon, essential oil of ginger, essential oil of black pepper, essential oil of pimento leaves, essential oil of peppermint and essential oil of clove, and a mixture or mixtures thereof.

For example, the agents for promoting cutaneous capillary circulation act, after topical application to the lips, via stimulation of vasodilation and/or an anticoagulant effect and/or an antihypertensive effect.

For instance, as agents that act via stimulation of vasodilation and/or an anticoagulant effect and/or an antihypertensive effect, mention may be made of:
  antihypertensive agents; such as potassium channel openers;
  phosphodiesterase inhibitors;
  flavonoids or flavoglycosides;
  glucosides;
  plant extracts with vasodilatory properties;
  vasodilatory peptides; and
  other vasodilators.

Antihypertensive Agents

Examples that may be mentioned include thiazides; angiotensin receptor inhibitors, for instance losartan or candesartan; prostaglandins, for example of type E and prostacyclins; ACE inhibitors, for instance captopril or ramipril; potassium channel openers, such as minoxidil, cromakalim, diazoxide, nicorandil, pinacidil and derivatives thereof; calcium channel blockers, such as nifedipine, verapamil, diltiazem or amlopidine; adrenergic receptor blockers, such as niacin (nicotinic acid), prazosin and hydralazine; muscarine acetylcholine receptor activators.

Phosphodiesterase Inhibitors

Examples that may be mentioned include type V phosphodiesterase inhibitors such as visnadine and esculoside, icarine and derivatives thereof or extracts containing it, as described in patent application WO 2005/004 858.

Flavonoids and Flavoglycosides

Examples that may be mentioned include Ginkgo flavoglycosides, amentflavone or dimeric flavones of Ginkgo biloba in free form or complexed with phospholipids, as described in patent application WO 2005/004 858; hesperidine, α-G-hesperidine, hesperidine methyl chalcone and rutosides (e.g.: β-hydroxyethyl-rutoside and trimethyl-rutoside).

Glucosides

Mention may be made for example of escin, escin beta-sitosterol, adenosine or ATP (adenosine triphosphate); esculoside, hesperidine, alpha-G-hesperidine and rutosides (e.g.: beta-hydroxyethyl-rutoside and trimethyl-rutoside).

Plant Extracts with Vasodilatory Properties

Examples that may be mentioned include Corsican everlasting (*Helichrysum italicum*) as described for example in patent application WO 03/018 730; extracts of blackcurrant (*Ribes nigrum*), of mistletoe, of epimedium (*Epimedium grandiflora*), of kiwi (*Actinidia chinensis* L.), of cypress (*Cupressus sempervirens*), of melilot (*Melissa officinalis*), of periwinkle (*Vinca minora*), of *Centella asiatica*, of *Terminalia sericea* (sericoside), extracts of calendula, extracts of arnica and extracts of *Ammi visnagi*.

Vasodilatory Peptides

Mention may be made of CGRP (peptides derived from the calcitonin gene), substance P (a decapeptide released by a nerve ending) or VIP (vasoactive intestinal polypeptide) as described in patent application EP 225 639, the content of which is incorporated into the present patent application by reference.

Other Vasodilators

Examples that may be mentioned include nicotinic acid (niacin) and derivatives thereof, for instance nicotinic acid esters, for example xanthinol nicotinate, inositol nicotinate; salicylic acid and esters thereof; dihydro-ergotoxine methanesulfonate; dihydro-ergocornine methanesulfonate, dihydro-ergocristine methanesulfonate, cinnarizine, vincamine, pentoxifylline, bamethane sulfate, bencyclane hydrogenofumarate and beta-pyridylcarbinol.

Mention may also be made of nitrogen monoxide (NO) donors or precursors and non-polymeric NO liberators; stimulators of NO synthase (NOS) synthesis and/or activity, and mixtures thereof.

Temperature Regulators

The temperature regulator may be a refreshing agent or a heating agent.

Examples of compounds with a refreshing effect that are known include menthol or plant extracts and/or essential oils of mint, of Aloe vera or of ginseng.

The refreshing agent may comprise an endothermic organic salt, for instance potassium chloride, mint or a derivative thereof, for instance menthol, peppermint, wintergreen, menthone, menthyl lactate, spearmint, mint oil, menthane derivatives, for instance N-substituted menthane carboxamides and for example N-ethyl P-menthane carboxamide-3, 3-(1-menthoxy)propane-1,2-diol, p-menthane-3,8-diol, menthyl succinate and alkaline-earth metal salts thereof, and mixtures thereof, or a nitrogenous compound such as urea.

Examples of heating agents that are known include camphor and plant extracts or essential oils of eucalyptus or of ginseng.

These compounds are generally used in concentrations ranging from 0.1% to 10% of the total weight of the composition.

The composition of the invention may be in solid, pasty or more or less fluid liquid form. It may be a solid or soft anhydrous gel, a liquid oily phase or a foam.

According to one variant of the invention, the compositions may contain less than 5% by weight, less than 3% by weight or less than 1% by weight of water, or are even free of water, i.e. anhydrous.

Solvent Phase

Generally, the composition according to the invention comprises at least one non-aqueous solvent phase.

This phase is capable of forming a continuous film and contains, as its name indicates, at least one non-aqueous organic solvent, which is for example a compound that is water-insoluble and liquid at room temperature and atmospheric pressure.

For the purposes of the invention, the term "volatile compound" means any compound (or non-aqueous medium) capable of evaporating on contact with keratin materials or the lips in less than one hour, at room temperature and atmospheric pressure. The volatile compound is a volatile cosmetic compound, which is liquid at room temperature, for example having a non-zero vapour pressure, at room temperature and atmospheric pressure, for instance having a vapour pressure ranging from 0.13 Pa to 40 000 Pa ($10^{-3}$ to 300 mmHg), ranging from 1.3 Pa to 13 000 Pa (0.01 to 100 mmHg) or ranging from 1.3 Pa to 1300 Pa (0.01 to 10 mmHg).

In contrast, the term "non-volatile compound" means a compound which remains on keratin materials or the lips, at room temperature and atmospheric pressure, for at least several hours and which for example has a vapour pressure of less than $10^{-3}$ mmHg (0.13 Pa).

The volatile compound that is water-insoluble and liquid at room temperature is for example a cosmetically acceptable oil (fatty substance that is liquid at 25° C. and atmospheric pressure) or organic solvent. The term "cosmetically acceptable" means a compound whose use is compatible with application to keratin materials.

The volatile oils may be hydrocarbon-based oils, silicone oils or fluoro oils, or mixtures thereof.

The term "hydrocarbon-based oil" means an oil mainly containing hydrogen and carbon atoms and possibly oxygen, nitrogen, sulfur or phosphorus atoms. The volatile hydrocarbon-based oils may be chosen from hydrocarbon-based oils containing from 8 to 16 carbon atoms, such as branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar® or Permethyl®, branched $C_8$-$C_{16}$ esters and isohexyl neopentanoate, and mixtures thereof. Other volatile hydrocarbon-based oils, for instance petroleum distillates, for example those sold under the name Shell Solt® by the company Shell, may also be used.

Volatile oils that may also be used include volatile silicones, for instance volatile linear or cyclic silicone oils, for example those with a viscosity <8 centistokes and for instance containing from 2 to 10 silicon atoms, these silicones optionally comprising alkyl or alkoxy groups containing from 1 to 22 carbon atoms. As volatile silicone oils that may be used in the invention, mention may be made for example of octamethylcyclotetrasiloxane, decamethylcyclopentasiloxane, dodecamethylcyclo-hexasiloxane, heptamethylhexyltrisiloxane, heptamethyloctyltrisiloxane, hexamethyl-disiloxane, octamethyltrisiloxane, decamethyltetrasiloxane and dodecamethyl-pentasiloxane, and mixtures thereof.

The non-aqueous solvent phase may also comprise at least one non-volatile compound that is water-insoluble and liquid at room temperature, for example at least one non-volatile oil, which may be chosen for instance from non-volatile and for example glossy hydrocarbon-based oils and/or silicone oils and/or fluoro oils.

Non-volatile hydrocarbon-based oils that may for example be mentioned include:

hydrocarbon-based oils of plant origin, such as triesters of fatty acids and of glycerol, the fatty acids of which may have varied chain lengths from $C_4$ to $C_{24}$, these chains possibly being linear or branched, and saturated or unsaturated; these oils are for instance wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil or musk rose oil; or caprylic/capric acid triglycerides, for instance those sold by the company Stéarineries Dubois or those sold under the names Miglyol 810®, 812® and 818® by the company Dynamit Nobel;

synthetic ethers containing from 10 to 40 carbon atoms;

linear or branched hydrocarbons of mineral or synthetic origin, such as petroleum jelly, polydecenes, hydrogenated polyisobutene for example with a high molecular weight such as parleam, and squalane, and mixtures thereof;

synthetic esters, for instance oils of formula $R_1COOR_2$ in which $R_1$ represents a linear or branched fatty acid residue containing from 1 to 40 carbon atoms and $R_2$ represents a hydrocarbon-based chain, which is for example branched, containing from 1 to 40 carbon atoms, on condition that $R_1+R_2$ 10, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate or diisostearyl malate; and pentaerythritol esters;

fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid or linolenic acid; and mixtures thereof.

The non-volatile silicone oils that may be used in the composition according to the invention may be non-volatile polydimethylsiloxanes (PDMS), polydimethylsiloxanes comprising alkyl or alkoxy groups, which are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyltrimethyl-siloxysilicates.

The fluoro oils that may be used in the invention are for example fluorosilicone oils, fluoro polyethers and fluorosilicones as described in document EP-A-847 752.

Thickening/Structuring Agent

The compositions according to the invention may be in anhydrous thickened form, for example in the form of a stick, for instance when it is intended for application to the lips. They may be thickened with at least one thickener selected from the group consisting of fatty-phase gelling agents, waxes, pasty fatty substances and fillers, and mixtures thereof.

Fatty-phase gelling agents that may be mentioned include optionally modified clays, for instance hectorites modified with a $C_{10}$ to $C_{22}$ fatty acid ammonium chloride, for instance hectorite modified with distearyldimethylammonium chloride; silica; partially or totally crosslinked elastomeric organopolysiloxanes of three-dimensional structure, for instance those sold under the names KSG6, KSG16 and KSG18 from Shin-Etsu, Trefil E-505C or Trefil E-506C from Dow Corning, Gransil SR-CYC, SR DMF 10, SR-DC556, SR 5CYC gel, SR DMF 10 gel and SR DC 556 Gel® from Grant Industries and SF 1204 and JK 113 from General Electric; galactomannans comprising from one to six and for example from two to four hydroxyl groups per saccharide, substituted with a saturated or unsaturated alkyl chain, for instance guar gum alkylated with $C_1$ to $C_6$ and for example $C_1$ to $C_3$ alkyl chains, for instance ethyl guar with a degree of substitution of 2 to 3, such as the product sold by the company Aqualon under the name N-Hance-AG; gums and for example silicone gums, for instance PDMSs with a viscosity >500 000 centistokes and/or a molecular weight of greater than or equal to 200 000 g/mol.

Silicone polyamides of the polyorganosiloxane type such as those described in documents U.S. Pat. No. 5,874,069, U.S. Pat. No. 5,919,441, U.S. Pat. No. 6,051,216 and U.S. Pat. No. 5,981,680 may also be used.

These silicone polymers may belong to the following two families:
polyorganosiloxanes comprising at least two groups capable of establishing hydrogen interactions, these two groups being located in the polymer chain, and/or
polyorganosiloxanes comprising at least two groups capable of establishing hydrogen interactions, these two groups being located on grafts or branches.

These gelling agents are used, for example, in concentrations of from 0.2% to 15% of the total weight of the composition.

The composition may also contain at least one wax.

For the purposes of the present invention, the term "wax" means a lipophilic fatty compound, which is solid at room temperature (25° C.), with a reversible solid/liquid change of state, having a melting point of greater than 30° C. that may be up to 200° C., a hardness of greater than 0.5 MPa, and having in the solid state an anisotropic crystal organization. By bringing the wax to its melting point, it is possible to make it miscible with oils and to form a microscopically homogeneous mixture, but on returning the temperature of the mixture to room temperature, recrystallization of the wax in the oils of the mixture is obtained.

The waxes that may be used in the invention are compounds that are solid at room temperature, which are intended to structure the composition for example in stick form; they may be hydrocarbon-based waxes, fluoro waxes and/or silicone waxes and may be of plant, mineral, animal and/or synthetic origin. For instance, they have a melting point of greater than 40° C. and better still greater than 45° C.

As waxes that may be used in the invention, mention may be made of those generally used in cosmetics: they are for example of natural origin, for instance beeswax, carnauba wax, candelilla wax, ouricoury wax, Japan wax, cork fibre wax, sugarcane wax, rice wax, montan wax, paraffin, lignite wax or microcrystalline wax, ceresin or ozokerite, and hydrogenated oils, for instance jojoba oil; synthetic waxes, for instance the polyethylene waxes derived from the polymerization or copolymerization of ethylene and Fischer-Tropsch waxes, or alternatively fatty acid esters, for instance octacosanyl stearate, glycerides that are solid at 40° C. and better still at 45° C., silicone waxes, for instance alkyl or alkoxy dimethicones containing an alkyl or alkoxy chain of 10 to 45 carbon atoms, and poly(di)methylsiloxane esters that are solid at 40° C., the ester chain of which contains at least 10 carbon atoms; and mixtures thereof.

The compositions according to the invention may for example contain polyethylene wax with a weight-average molecular mass of between 300 and 700 and for instance equal to 500 g/mol.

As a guide, the wax may represent from 0.01% to 50%, from 2% to 40% or from 5% to 30% of the total weight of the composition.

The compositions may also contain at least one pasty compound.

For the purposes of the present invention, the term "pasty substance" is intended to denote a lipophilic fatty compound, with a reversible solid/liquid change of state, comprising at a temperature of 23° C. a liquid fraction and a solid fraction. The term "pasty substance" also means polyvinyl laurate.

The pasty compound is for example selected from the group consisting of:
lanolin and its derivatives,
polymeric or non-polymeric fluoro compounds,
polymeric or non-polymeric silicone compounds,
vinyl polymers, for instance:
olefin homopolymers
olefin copolymers
hydrogenated diene homopolymers and copolymers
homopolymeric or copolymeric linear or branched oligomers of alkyl (meth)acrylates for example containing a $C_8$-$C_{30}$ alkyl group
homopolymeric and copolymeric oligomers of vinyl esters containing $C_8$-$C_{30}$ alkyl groups
homopolymeric and copolymeric oligomers of vinyl ethers containing $C_8$-$C_{30}$ alkyl groups
liposoluble polyethers resulting from polyetherification between one or more $C_2$-$C_{100}$ and for instance $C_2$-$C_{50}$ diols
esters
and mixtures thereof.

Among the liposoluble polyethers that may be suitable for the present invention are for example copolymers of ethylene oxide and/or of propylene oxide with $C_6$-$C_{30}$ long-chain alkylene oxides, for instance such that the weight ratio of the ethylene oxide and/or of the propylene oxide to the alkylene oxides in the copolymer is from 5:95 to 70:30. In this family, mention may be made for example of copolymers such that the long-chain alkylene oxides are arranged in blocks with a mean molecular weight of from 1000 to 10 000, for example a polyoxyethylene/polydodecyl glycol block copolymer such as the ethers of dodecanediol (22 mol) and of polyethylene glycol (45 EO) sold under the brand name Elfacos ST9 by Akzo Nobel.

Among the pasty esters that may be suitable for the present invention mention may for example be made of:
- esters of an oligomeric glycerol, such as diglycerol esters, for instance condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, such as like those sold under the brand name Softisan 649 by the company Sasol,
- the arachidyl propionate sold under the brand name Waxenol 801 by Alzo,
- phytosterol esters,
- non-crosslinked polyesters resulting from the polycondensation between a linear or branched $C_4$-$C_{50}$ dicarboxylic or polycarboxylic acid and a $C_2$-$C_{50}$ diol or polyol, other than the polyester described above,
- aliphatic esters of an ester resulting from the esterification of an ester of an aliphatic hydroxycarboxylic acid with an aliphatic monocarboxylic acid; and mixtures thereof, for instance
  - the ester resulting from the esterification reaction of hydrogenated castor oil with isostearic acid in proportions of 1 to 1 (1/1) or hydrogenated castor oil monoisostearate,
  - the ester resulting from the esterification reaction of hydrogenated castor oil with isostearic acid in proportions of 1 to 2 (1/2) or hydrogenated castor oil diisostearate,
  - the ester resulting from the esterification reaction of hydrogenated castor oil with isostearic acid in proportions of 1 to 3 (1/3) or hydrogenated castor oil triisostearate,
  - and mixtures thereof.

Among the pasty compounds of plant origin that may for example be chosen mention may be made of a mixture of soybean sterols and of oxyethylenated (5 EO) oxypropylenated (5 PO) pentaerythritol, sold under the reference Lanolide by the company Vevy.

The pasty compound may for instance represent from 1% to 99%, from 1% to 60%, from 2% to 30% or from 5% to 20% by weight of the composition.

As stated previously, the compositions according to the invention may also comprise one or more fillers, for example in a content ranging from 0.01% to 50% by weight, or ranging from 0.01% to 30% by weight relative to the total weight of the composition.

The term "fillers" should be understood as meaning white or colourless, mineral or synthetic particles of any form, which are insoluble in the medium of the composition irrespective of the temperature at which the composition is manufactured. These fillers serve for instance to modify the rheology or the texture of the composition.

The fillers may be mineral or organic of any form, platelet-shaped, spherical or oblong. Mention may be made of talc, mica, silica, kaolin, polyamide (Nylon®) powders (Orgasol® from Atochem), poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or of acrylic acid copolymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and for example from 12 to 18 carbon atoms, for example zinc stearate, magnesium stearate or lithium stearate, zinc laurate or magnesium myristate, and Polypore® L200 (Chemdal Corporation). Mention may also be made of silica-based fillers, for instance Aerosil 200, Aerosil 300; Sunsphere L-31 and Sunsphere H-31 sold by Asahi Glass; Chemicelen sold by Asahi Chemical; composites of silica and of titanium dioxide, for instance the TSG series sold by Nippon Sheet Glass. Finally, mention may be made of polyurethane powders, such as powders of crosslinked polyurethane comprising a copolymer, the said copolymer comprising trimethylol hexyllactone. For instance, it may be a polymer of hexamethylene diisocyanate/trimethylol hexyllactone. Such particles are for instance commercially available, for example, under the name Plastic Powder D-400® or Plastic Powder D-800® from the company Toshiki.

Dyestuff

For example, the compositions of the invention comprise at least one dyestuff, which may be selected from the group consisting of dyes, pigments and nacres, and mixtures thereof. This dyestuff may represent from 0.001% to 98%, from 0.5% to 85% or from 1% to 60% of the total weight of the composition.

For obvious reasons, these dyestuffs are used in the compositions according to the invention so as not to harm the effect more particularly desired according to the invention, and which is especially directed towards affording a natural makeup effect.

For a composition in paste or cast form such as lipsticks or body makeup products, from 0.5% to 50%, from 2% to 40% or from 5% to 30% of dyestuff may be generally used relative to the total weight of the composition.

The dyes are for example liposoluble dyes, although water-soluble dyes may be used. The liposoluble dyes are, for example, Sudan red, D & C Red 17, D & C Green 6, β-carotene, soybean oil, Sudan brown, D & C Yellow 11, D & C Violet 2, D & C Orange 5, quinoline yellow and annatto. They may represent from 0 to 20% and better still from 0.1% to 6% of the weight of the composition. The water-soluble dyes are for instance beetroot juice and methylene blue, and may represent from 0.1% to 6% by weight of the composition (if present).

The term "pigments" should be understood as meaning white or coloured, mineral or organic particles that are insoluble in the liquid fatty phase, which are intended to colour and/or opacify the composition. The term "nacres" should be understood as meaning iridescent particles, for example produced by certain molluscs in their shell or alternatively synthesized.

The pigments may be present in the composition in a proportion of from 0.05% to 30% and for instance in a proportion of from 2% to 20% of the weight of the final composition. As mineral pigments that may be used in the invention, mention may be made of titanium oxide, zirconium oxide or cerium oxide, and also zinc oxide, iron oxide or chromium oxide and ferric blue. Among the organic pigments that may be used in the invention, mention may be made of carbon black, and barium, strontium, calcium (D & C Red No. 7) and aluminium lakes.

The nacres may be present in the composition in a proportion of from 0.001% to 20%, or for example from 1% to 15% of the total weight of the composition. Among the nacres that may be used in the invention, mention may be made of mica coated with titanium oxide, with iron oxide, with natural pigment or with bismuth oxychloride, such as coloured titanium mica.

The composition for instance contains goniochromatic pigments, for example multilayer interference pigments, and/or reflective pigments. These two types of pigment are described in patent application FR 02/09246, the content of which is incorporated into the present patent application by reference.

The compositions according to the invention may also contain ingredients commonly used in cosmetics, such as vitamins, trace elements, softeners, sequestrants, fragrances, basifying or acidifying agents, preserving agents, sunscreens, surfactants, antioxidants, propellants and film-forming polymers, or mixtures thereof.

Needless to say, a person skilled in the art will take care to select this or these optional additional compound(s), and/or the amount thereof, such that the advantageous properties of the corresponding composition according to the invention are not, or are not substantially, adversely affected by the envisaged addition.

The compositions according to the invention may be manufactured via the known processes generally used in cosmetics or dermatology. For example, they may be obtained by heating the various constituents to the melting point of the highest-melting waxes, followed by pouring the molten mixture into a mould (dish or finger stall). They may also be obtained by extrusion, as described in patent application EP-A-667 146.

The composition of the invention may be in solid, pasty or more or less fluid liquid form. It may be for example a gloss or a soft paste for caring for or making up the lips.

The invention is illustrated in greater detail in the examples that follow. The percentages are given on a weight basis.

EXAMPLE: GLOSS

| Components | Concentration (mass %) |
|---|---|
| Collagen spheres and chondroitin sulfate (Coletica) | 0.10 |
| N-Ethyl p-menthane carboxamide-3 | 0.10 |
| Di-tert-butyl-4-hydroxytoluene | 0.10 |
| Glyceryl caprylate/caprate[1] | 1.50 |
| Alumina-treated rutile titanium oxide/silica/trimethylolpropane | 0.10 |
| Mixture of polydimethylsiloxane and of hydrated silica | 0.20 |
| Fragrance | 0.30 |
| Hydrophobic fumed silica surface-treated with dimethylsilane | 5.00 |
| 1,2-Octanediol [2] | 0.50 |
| Polybutene (MW 920) | 29.25 |
| Mica | 1.00 |
| Preserving agents | 0.40 |
| 2-Octyldodecanol | 10.00 |
| Essential oil of cinnamon | 0.90 |
| Essential oil of ginger | 0.40 |
| Isononyl isononanoate | 4.00 |
| Tridecyl trimellitate | 13.45 |
| Polybutene (MW: 1290) | qs 100 |

[1] Capmul MCM from Abitec
[2] Dermosoft Octiol from Straetmans

After applying the above gloss to the lips, swelling of the lips is observed, affording an appreciable fleshy or pouty effect that is perceptible to the user.

The invention claimed is:

1. A cosmetic composition for caring for and/or making up the skin and/or the lips, containing, in a physiologically acceptable medium:
at least one active agent consisting of at least one glycol with a $C_4$-$C_{16}$ hydrocarbon-based chain and/or at least one hydroxylated ester resulting from the esterification of polyol and of carboxylic acid(s),
a solvent phase consisting of at least one non-volatile hydrocarbon-based oil and/or silicone oil, optionally further including at least one volatile hydrocarbon-based oil and/or silicone oil;
at least one additional agent selected from the group consisting of N-substituted menthane carboxamides; and
less than 5% by weight of water;
the polyol being selected from the group consisting of glycerol, butyl diglycol, polyglyceryle-3 diisostearate, castor oil, glycol, ethylene glycol, propylene glycol, hexylene glycol, isoprene glycol, butylene glycol and pentylene glycol;
the carboxylic acid(s) being selected from the group consisting of $C_7$-$C_{10}$ non-hydroxylated acid;
the composition not comprising any fluoro oil; and
the composition comprising from 0.05% to 20% by weight of the active agent relative to a total weight of the composition.

2. The composition according to claim 1, wherein the at least one hydroxylated ester is a hydroxylated diester.

3. The composition according to claim 1, wherein the at least one hydroxylated ester bears at least two free OH function(s) on its alcohol residue.

4. The composition according to claim 1, wherein the polyol is selected from the group consisting of propylene glycol and glycerol.

5. The composition according to claim 1, wherein the acid is selected from the group consisting of heptanoic acid, caprylic acid and capric acid.

6. The composition according to claim 1, wherein the at least one hydroxylated ester is selected from the group consisting of monoglyceryl and/or diglyceryl caprylates, monoglyceryl and/or diglyceryl heptanoates, monoglyceryl and/or diglyceryl caprates, propylene glycol caprylates and propylene glycol heptanoate, and mixtures thereof.

7. The composition according to claim 1, wherein the at least one hydroxylated ester comprises at least monoglyceryl caprylate.

8. The composition according to claim 1, wherein the at least one glycol contains a $C_7$-$C_{14}$ hydrocarbon-based chain.

9. The composition according to claim 1, wherein the at least one glycol contains a $C_6$-$C_{14}$, hydrocarbon-based chain.

10. The composition according to claim 1, wherein the at least one glycol is caprylyl glycol.

11. The composition according to claim 1, said composition being suitable for topical application.

12. The composition according to claim 1, in the form of a care base, a care cream, a makeup base, a tinted cream, a foundation, a lipstick, a liquid gloss, a lipstick paste, a lip contour pencil, a lip balm or a lip varnish.

13. The cosmetic composition according to the claim 1, said composition being anhydrous.

14. The composition according to claim 1, said composition further comprising at least one dyestuff.

15. The composition according to claim 1, said composition further comprising at least one thickener selected from the group consisting of waxes and pasty fatty substances.

16. The composition according to claim 1, said composition further containing at least one filler.

17. A cosmetic method for reinforcing the natural flesh tint of skin and/or lips and/or the natural volume of lips, comprising at least the step of applying on the skin and/or lips a composition as defined in claim 1.

18. A cosmetic method for giving the skin of a face, a healthy appearance, comprising at least the step of applying on the skin a composition as defined in claim 1.

19. A cosmetic method for homogenizing and/or clarifying the complexion and/or for reducing the hazy complexion effect, comprising at least the step of applying on skin a composition as defined in claim 1.

20. A cosmetic method for increasing the size and/or volume of lips and/or for modeling lips and/or making lips smoother, comprising at least the step of applying on the lips a composition as defined in claim 1.

21. A cosmetic method for stimulating the natural coloration of lips, comprising at least the step of applying on the lips a composition as defined in claim 1.

22. A cosmetic method for giving a healthy complexion effect, comprising at least the step of applying on skin a composition as defined in claim 1.

23. A method for making up lips, comprising application to the lips a composition as defined in claim 1.

* * * * *